United States Patent
Wheeler et al.

(10) Patent No.: US 12,059,575 B2
(45) Date of Patent: Aug. 13, 2024

(54) COMPLIANT OPTRODES FOR MONITORING AND STIMULATING BIOLOGICAL TISSUE WITH PATTERNED LIGHT

(71) Applicant: The Charles Stark Draper Laboratory, Inc., Cambridge, MA (US)

(72) Inventors: Jesse J. Wheeler, Revere, MA (US); Joseph J. Register, Cambridge, MA (US); Parshant Kumar, Cambridge, MA (US); Carlos A. Segura, Cambridge, MA (US); Charles A. Lissandrello, Cambridge, MA (US); John J. LeBlanc, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/811,429

(22) Filed: Nov. 13, 2017

(65) Prior Publication Data

US 2018/0133506 A1   May 17, 2018

Related U.S. Application Data

(60) Provisional application No. 62/421,781, filed on Nov. 14, 2016.

(51) Int. Cl.
*A61N 5/06* (2006.01)
*A61B 5/00* (2006.01)

(52) U.S. Cl.
CPC .......... *A61N 5/0622* (2013.01); *A61B 5/0031* (2013.01); *A61N 5/0601* (2013.01); *A61N 2005/0612* (2013.01); *A61N 2005/063* (2013.01)

(58) Field of Classification Search
CPC ............ A61N 5/0622; A61N 2005/063; A61N 2005/0612; A61N 5/0601; A61B 5/0031
See application file for complete search history.

(56) References Cited

U.S. PATENT DOCUMENTS

| | | | |
|---|---|---|---|
| 6,243,525 B1 * | 6/2001 | Luizink ................. | G02B 6/125 385/131 |
| 8,263,986 B2 * | 9/2012 | Hajj-Hassan ...... | G01N 21/7703 257/14 |
| 8,475,506 B1 * | 7/2013 | Bendett ................ | A61N 5/0622 607/88 |

(Continued)

OTHER PUBLICATIONS

Yanina Grinberg, Fascicular Perineurium Thickness, Size, and Position Affect Model Predictions of Neural Excitation, Dec. 2008, IEEE Trans Neural Syst Rehabil Eng., 16(6), 572-581 (Year: 2008).*

Amagiwa s et al: 11 Flexible optrode array: Parylene-film waveguide arrays with microelectrodes—for optogenetics11 , 2015 Transducer 2015 18th International Conference On Solid-State Sensors, Actuators and Microsystems (Transducers), IEEE Jun. 21, 2015 (Jun. 21, 2015), pp. 277-280, XP033189273, DOI: 10.1109/TRANSDUCERS.2015.7180915 [retrieved on Aug. 5, 2015] abstract; figure 1,p. 278, left-hand column.

(Continued)

*Primary Examiner* — P. Kathryn Wright
*Assistant Examiner* — Curtis A Thompson
(74) *Attorney, Agent, or Firm* — FOLEY & LARDNER LLP

(57) ABSTRACT

A device can include a first compliant optrode. The first compliant optrode can be introduced into a tissue sample and can include a stack of flexible waveguide materials providing a first optical interface. The stack of flexible waveguide materials can have a thickness of less than about 100 microns. The first compliant optrode can be linear and can be configured to bend at a turn radius of less than about 300 microns.

11 Claims, 7 Drawing Sheets

(56) References Cited

U.S. PATENT DOCUMENTS

| | | | | |
|---|---|---|---|---|
| 8,676,334 | B2* | 3/2014 | Youn | A61N 1/36003 607/48 |
| 8,747,447 | B2* | 6/2014 | Stafford | A61N 1/36039 607/89 |
| 2004/0069717 | A1 | 4/2004 | Laurell et al. | |
| 2010/0074579 | A1* | 3/2010 | Fujii | G02B 6/02033 385/31 |
| 2010/0166362 | A1* | 7/2010 | Fujii | G02B 6/4214 385/14 |
| 2011/0087311 | A1* | 4/2011 | Zorzos | A61N 5/0601 607/89 |
| 2011/0112591 | A1* | 5/2011 | Seymour | A61B 5/0084 607/3 |
| 2011/0295345 | A1* | 12/2011 | Wells | A61N 5/0601 607/89 |
| 2012/0051691 | A1* | 3/2012 | Zhang | G01C 19/721 385/14 |
| 2012/0287420 | A1* | 11/2012 | McLaughlin | A61B 5/0084 356/72 |
| 2013/0030274 | A1* | 1/2013 | Jamieson | A61B 5/0084 600/377 |
| 2013/0079615 | A1* | 3/2013 | Yoon | A61B 5/04001 600/377 |
| 2013/0183015 | A1* | 7/2013 | Mori | G02B 6/122 385/126 |
| 2014/0148886 | A1* | 5/2014 | Tsang | A61N 1/0551 607/118 |
| 2014/0288541 | A1* | 9/2014 | Eshkol | A61B 17/32056 606/7 |
| 2015/0018901 | A1* | 1/2015 | Li | A61N 5/0601 607/92 |
| 2015/0202456 | A1* | 7/2015 | Andersen | A61K 38/177 604/20 |
| 2015/0374975 | A1* | 12/2015 | Callegari | A61N 1/0556 29/874 |
| 2016/0004010 | A1* | 1/2016 | Miller | G02B 6/138 118/620 |
| 2016/0066789 | A1* | 3/2016 | Rogers | A61N 1/05 604/20 |
| 2016/0163928 | A1* | 6/2016 | Tsukihara | H01L 33/325 257/101 |
| 2019/0003898 | A1* | 1/2019 | Dehkhoda | G01K 7/427 |

OTHER PUBLICATIONS

International Search Report and The Written Opinion of the International Searching Authority dated Feb. 6, 2018 for application No. PCT/US2017/061382.

International Preliminary Report on Patentability dated May 23, 2019 for application. No. PCT/US2017/061382.

Amagiwa s et al: 11 Flexible optrode array: Parylene-film waveguide arrays with microelectrodes—for optogenetics11 , 2015 TRANSDUCERS 2015 18TH International Conference On Solid-State Sensors, Actuators and Microsystems (Transducers), IEEE, Jun. 21, 2015 (jUN. 21, 2015), pp. 277-280, XP033189273, DOI: 10.1109/TRANSDUCERS.2015.7180915 [retrieved on Aug. 5, 2015] abstract; figure 1, p. 278, left-hand column.

Curtis D. Lee et al: "Mechanical Properties of Thin-Film Parylene-Metal-Parylene Devices", Frontiers in Mechanical Engineering, vol. 1, Sep. 8, 2015 (Sep. 8, 2015).

Jun-Hyoung Kim et al: "A curvature controlled flexible silicon micro electrode array to wrap neurons for signal analysis", Transducers 2009: 2009 International Solid-State Sensors, Actuators and Microsystems Conference; Denver, Colorado, USA, Jun. 21-25, 2009, IEEE, Piscataway, NJ, USA, Jun. 21, 2009 (Jun. 21, 2009), pp. 1810-1813.

Naoki Tanaka: "Researchers Develop Highly-flexible OLEO Light Source—Nikkei Technology Online",Jul. 26, 2013 (Jul. 26, 2013), XP055440632, Retrieved from the Internet: URL:http://techon.nikkeibp.co.jp/english/N EWS EN/20130730/295194/[retrieved on Jan. 12, 2018]the whole document.

The international Search Report and The Written Opinion of the International Searching Authority dtd Feb. 6, 2018 for application No. PCT/US2017/061382.

Transmittal of Copy of the International Preliminary Report on Patentability dated May 23, 2019 for application. No. PCT/US2017/061382.

Akhtar et al., "Characterizing the elastic properties of tissues", Materials Today, vol. 14, No. 3, Mar. 1, 2011 (Mar. 1, 2011), pp. 96-105, XP055718880, Amsterdam.NL, ISSN: 1369-7021, DOI: 10.1016/S1369-7021 (11)70059-1 (21 pages).

Examination Report for EP 17807984.4 dated Aug. 4, 2020 (5 pages).

European Action EP Appln. 17807984.4 dated Sep. 14, 2021.

* cited by examiner

COMPLIANT OPTRODES FOR MONITORING AND STIMULATING BIOLOGICAL TISSUE WITH PATTERNED LIGHT

CROSS-REFERENCE TO RELATED APPLICATION

This application claims priority to U.S. Provisional Patent Application No. 62/421,781 filed on Nov. 14, 2016 and titled "Compliant Optrodes for Monitoring and Stimulating Biological Tissue with Patterned Light," which is herein incorporated by reference in its entirety.

BACKGROUND

The field of optogenetics generally relates to sensitizing target neurons to light stimuli. For example, this can be achieved by inserting light-sensitive opsins using genetic techniques. After the target neurons have been sensitized to light, light pulses can be delivered to the target neurons to stimulate the target neurons. Typically, target neurons may be very small and may be surrounded by soft tissue. Thus, it can be difficult to bend and route light in a manner to introduce light stimuli to the neurons.

SUMMARY

One aspect of this disclosure is directed to a device that can include a first compliant optrode. The first compliant optrode can include a stack of flexible waveguide materials providing a first optical interface and configured to be introduced into a tissue sample. The stack of flexible waveguide materials can have a thickness of less than about 100 microns. The first compliant optrode can be substantially linear and can be configured to bend at a turn radius of less than about 300 microns.

In some implementations, the first compliant optrode can have at least one mechanical property selected to substantially match a corresponding mechanical property of the tissue sample. In some implementations, the tissue sample can include nerve tissue. In some implementations, the first optical interface can be configured to provide optical stimulation to at least a portion of the tissue sample.

In some implementations, the device can also include at least a second compliant optrode positioned adjacent to the first compliant optrode and providing a second optical interface. The first compliant optrode and the second compliant optrode can form a bundle within the device. In some implementations, the first compliant optrode can be configured to deliver a first optical output to a first activation zone of the tissue sample. The first optical output can include light directed towards the first activation zone in a first direction. In some implementations, the second compliant optrode is configured to deliver a second optical output to a second activation zone of the tissue sample. In some implementations, the second activation zone can substantially overlap with the first activation zone. In some implementations, the second activation zone can be spaced away from the first activation zone. In some implementations, the second optical output can include light directed towards the second activation zone in a second direction, different from the first direction.

In some implementations, the device can also include an electrode positioned adjacent to the first compliant optrode and providing an electrical interface. The first compliant optrode and the electrode can form a bundle within the device. In some implementations, the electrode can be defined by a metal layer included within the stack of flexible waveguide materials. In some implementations, the metal layer can have a thickness of less than about 50 microns.

In some implementations, the first compliant optrode can be configured to be inserted into a nerve fascicle included within the tissue sample. In some implementations, the first compliant optrode can be configured to be wrapped around a nerve fascicle included within the tissue sample. In some implementations, the first optical interface can be configured to receive an optical input corresponding to an optical response of the tissue sample.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

DETAILED DESCRIPTION

Figure 1A:
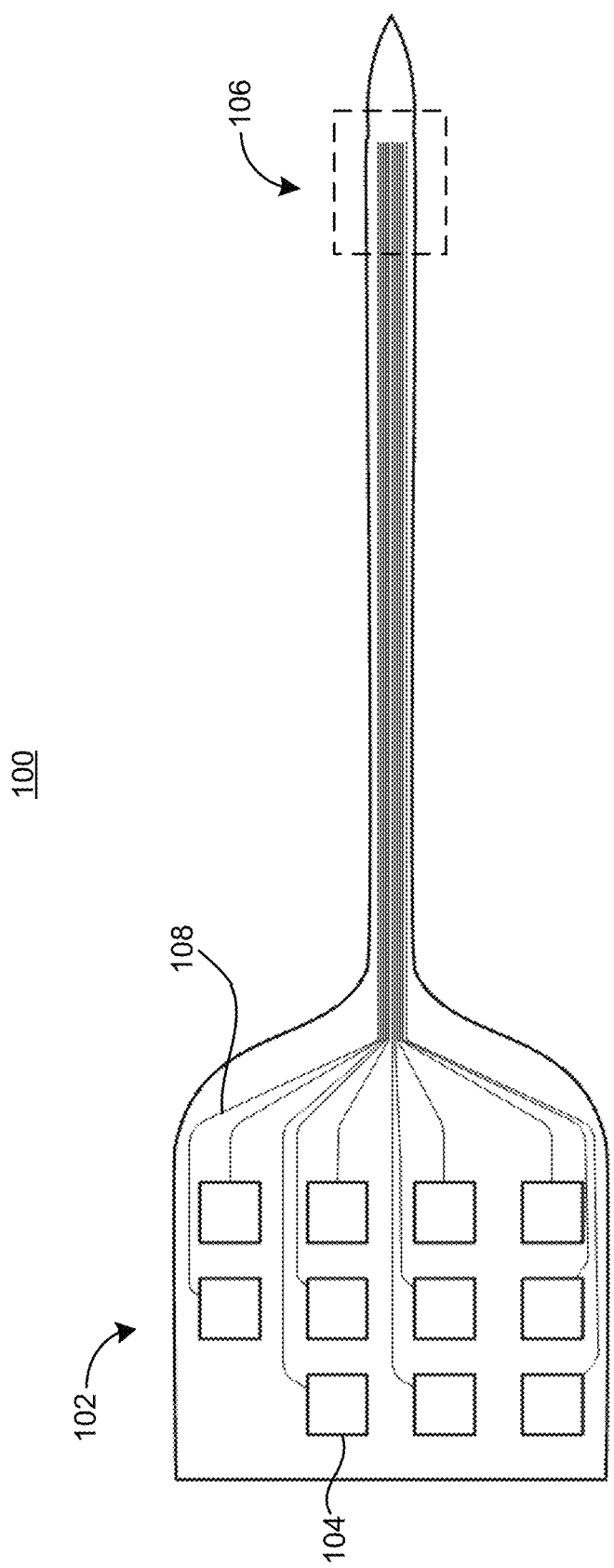
FIG. 1A illustrates a schematic of an example device, according to an illustrative implementation.

Following below are more detailed descriptions of various concepts related to, and implementations of compliant optrodes for monitoring and stimulating biological tissue with patterned light. The devices described in this disclosure can be used in optogenetic optrodes, light stimulation devices, imaging devices, endoscopes, and other types of optrodes. The various concepts introduced above and discussed in greater detail below may be implemented in any of numerous ways, as the described concepts are not limited to any particular manner of implementation. Examples of specific implementations and applications are provided primarily for illustrative purposes. As described above, the field of optogenetics can benefit from devices that can be configured to route light around tight turns in order to access small anatomical targets, such as targeted neural tissue. Traditional optical fibers can be efficient at transmitting light across distances, but are limited in their ability to bend light around small diameter turns, such as turns having a diameter of less than one millimeter.

This disclosure relates in part to optical waveguides that are thin and flexible, and that can bend light around such small turns. In some implementations, the waveguides can be formed from a stack of materials can include a polymer core and a cladding, which together create a large difference in refractive index. As a result, light can remain within the core even when bent around radii where standard glass fibers could fail. The materials can be integrated with other types of structures, such as microfluidic structures or electrical structures, such as electrodes. In some implementations, microfabricated waveguides may be thin and flexible, thereby allowing the waveguides to easily bend and wrap around small structures. For example, traditional optical fibers may be unable to bend light around turns that are smaller than a few millimeters, while the flexible optical waveguides described herein may be capable of bending light around turns of less than one millimeter.

In some implementations, compliant waveguide materials such as those describe herein may allow optrodes to wrap around structures and maintain robust interfaces by matching the mechanical properties of the surrounding soft tissue. Bending and routing light around tight turns can enable both miniaturization of arrays or of optical waveguides, as well as higher channel counts. In some implementations, a microfabricated waveguide stack may have a thickness of approximately 25 microns and may be configured to transmit light around diameters of 250 microns or less. In some implementations, optrodes also may be integrated with electrodes to allow for multimodal interfaces.

A variety of material stacks may be used for fabricating optrodes. In some implementations, a material stack may include a core material surrounded by a cladding material. In one example, the core may be formed from or may include ORMOCORE® (made available by Microresist), or poly(methyl methacrylate) (PMMA), SU-8, or poly(p-xylylene) polymers, and may be surrounded by a cladding formed from or including a material such as CYTOP™ (made available by Asahi Glass Company), CYCLOTENE™ (made available by Dow Chemical), TAFLON AF™ (made available by Chemours), or another fluoropolymer. In some implementations, flexible optical waveguides can be combined with electrodes, for example by inserting a metallization layer into the stack. This can be useful for biomedical interfaces where it may be desirable to combine both optical and electrical stimulation and monitoring.

In some implementations, intersecting beams of light from multiple optrode sites can be used to produce focused areas of intensity for light delivery and monitoring. Intersecting beams can be created, for example, by wrapping optrodes around tissue or by directionally steering beams of light from optrode sites. Directionally steered beams can be created by using multiple fixed-direction optical apertures or by actively shifting light direction from a single optical aperture. In some implementations, multiple fixed-direction optical apertures can be placed near to one another to create functional equivalents of single multi-directional apertures. Dynamically reshaped lenses, mirrors, and optical fibers can be used to emit and collect light to and from desired directions.

Figure 1B:
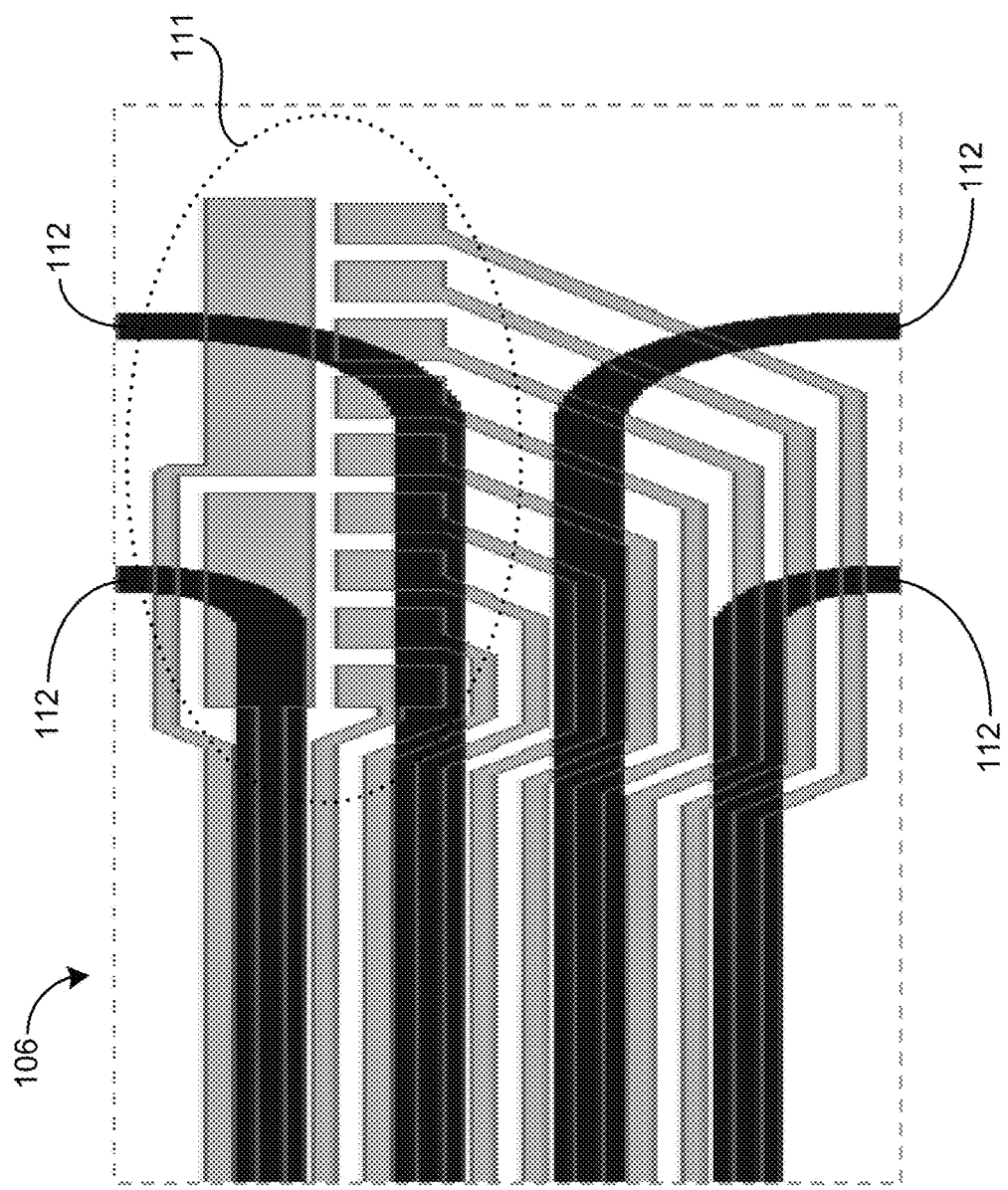
FIG. 1B illustrates an enlarged portion of the example device of FIG. 1A, according to an illustrative implementation.

FIG. 1A illustrates a schematic of an example device 100. A proximal end 102 of the device 100 includes a plurality of contact pads 104. Each of the contact pads 104 can be electrically coupled to an electrode or optrode site at the distal end 106 of the device 100 through an electrical trace 108. FIG. 1B illustrates an enlarged view of the distal end 106 of the device 100. FIGS. 1A and 1B are described together below. As shown in FIG. 1B, the distal end 106 of the device 100 includes a plurality of electrodes 111 and a plurality of optrodes 112. In some implementations, each optrode 112 can include a material stack forming a waveguide. The optrodes 112 can carry or transmit light from the proximal end 102 to the distal end 106 (in cases of projecting light from the distal end 106) or from the distal end 106 to the proximal end 102 (in cases of detecting light from the distal end 106).

In some implementations, the device 100 can include a stack of materials where the optrodes 112 are formed from a polymer core and a cladding. The polymer core and the cladding, together, create a large difference in refractive index. As a result, light can remain within the core (e.g., the optrodes 112) even when bent around radii where standard glass fibers could fail.

In some implementations, the materials of the device 100 can be patterned using, for example, photolithographic methods and can be integrated with other types of structures, such as microfluidic structures or electrical structures (e.g., the contact pads 104 and electrical traces 108). In some implementations, the microfabricated optrodes 112 may be thin and flexible to enable the optrodes 112 to easily bend and wrap around small structures without a substantial loss of light along the length of the optrodes 112. For example, traditional optical fibers may be unable to bend light around turns that are smaller than a few millimeters. However, the flexible optical waveguides described herein are capable of bending light around turns of less than one millimeter.

The optrodes 112 can be compliant in order to enable the device 100 to wrap around structures (e.g., soft tissue, nerves, etc.) while maintaining robust interfaces with the structures by matching the mechanical properties of the structures. For example, the optrodes 112 can be made from a stack of flexible materials, such as polymers, so that the optrodes can bend and flex at angles that could cause breakage for traditional glass fibers, which tend to be relatively rigid and brittle. Thus, unlike stiff optical waveguides, the compliant optrodes 112 can allow the device 100 to be a closer mechanical match to the modulus of soft tissue, which can allow the device 100 to more robustly integrate with tissue for chronic applications. Flexibility can also allow the device 100 to bend around tissue structures allowing easier delivery and routing of light through the tissue.

The material stack of the device 100 enables light to be bent around very fine structures (e.g., smaller than one millimeter), which can enable the device 100 to wrap around tissue, such as small nerves. The device 100 can be used to both deliver light and capture light for both stimulation and monitoring applications. In some implementations, stiff mechanical backings and a leader (e.g., a needle) can be used for inserting the device 100 and can be detached after insertion, leaving behind the device 100. The device 100 can be combined with optogenetic stimulation and monitoring techniques to selectively activate tissue (e.g. neural, cardiac, etc.). In some implementations, combining optical and electrical modes for stimulation and monitoring (e.g., via the electrodes 111 and the optrodes 112) can help to minimize undesirable artifacts caused by simultaneous stimulation and monitoring using only a single mode (e.g., only electrical or only optical). Bending and routing light around tight turns can enable both miniaturization of arrays or of the optrodes 112, as well as higher channel counts. In some implementations, the device 100 (and the waveguide stack) can have a thickness of less than about 350 µm, less than about 300 µm, less than about 250 µm, less than about 200 µm, less than about 150 µm, less than about 100 µm, less than about 50 µm, or less than about 25 µm. In some implementations, the electrodes 111 can be formed from metal layers that may be included within the waveguide stack. Such metal layers may have a thickness of less than about 100 µm, less than about 75 µm, less than about 50 µm, or less than about 25 µm.

It should be understood that the number and arrangement of the electrodes 111 and the optrodes 112 illustrated in FIG. 1B are illustrative only, and should not be interpreted as limiting the scope of this disclosure. For example, in some implementations, the device 100 can include more or fewer electrodes 111, or more or fewer optrodes 112, than are illustrated in FIG. 1B. In some implementations, the device 100 may include only electrodes 111 without any optrodes 112, or may include only optrodes 112 without any electrodes. In some implementations, the device 100 may include only a single optrode 112 or only a single electrode 111. In addition, the arrangement of optrodes 112 and electrodes 111 may be selected to be suitable for a particular application, and may differ from the particular arrangement depicted in FIG. 1B.

Figure 2A:
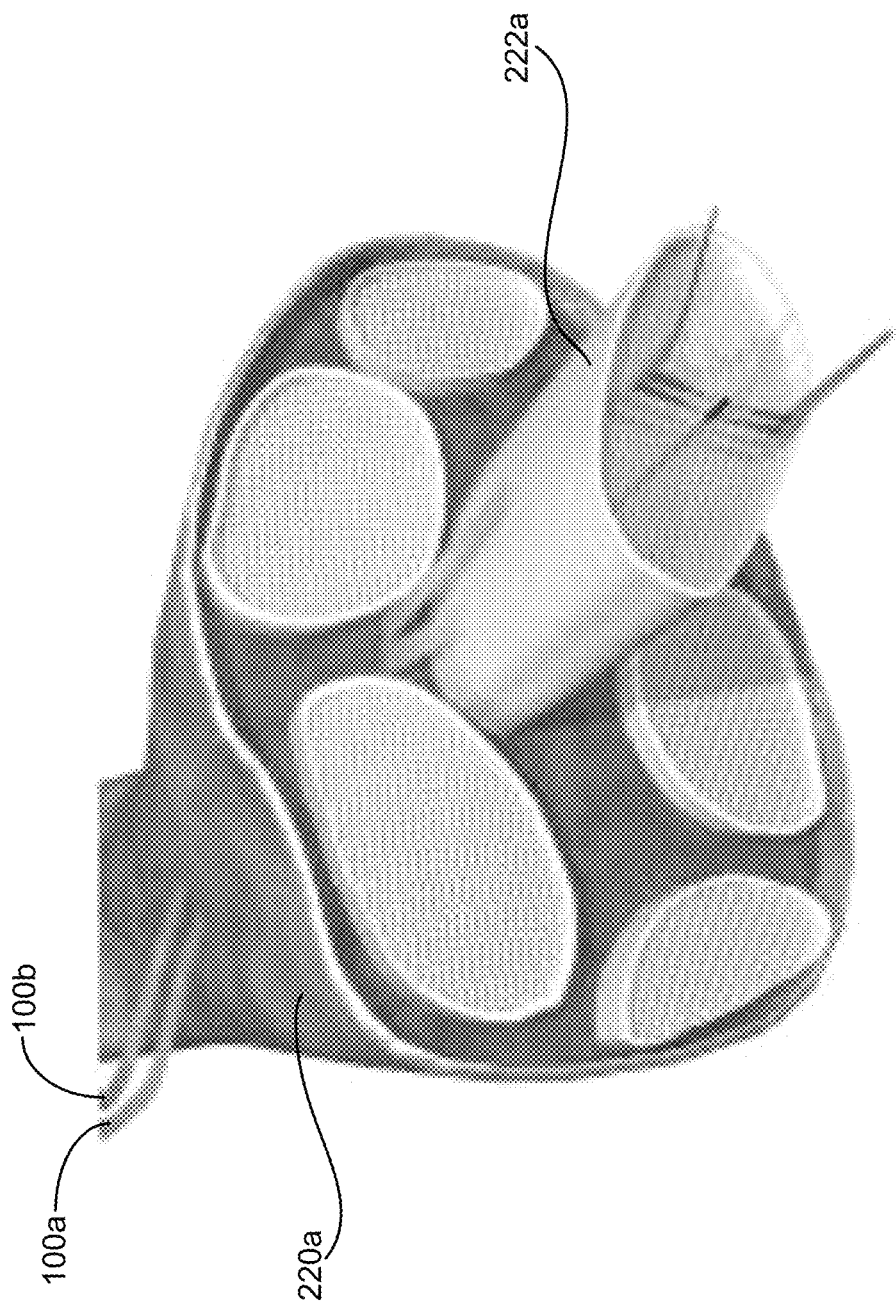
FIG. 2A illustrates a first example precision optogenetic interface, according to an illustrative implementation.

FIG. 2A illustrates a first example precision optogenetic interface, according to an illustrative implementation. As shown, two instances of the device 100 shown in FIG. 1A (labeled 100a and 100b) can be inserted into a tissue sample 220a. In this example, the tissue sample 220a is nerve tissue including several nerve fascicles, such as the nerve fascicle 222a. The devices 100a and 100b are small, thin, thread-like devices having very narrow cross-sections, as illustrated in FIG. 1A. In some implementations, the devices 100a and 100b are substantially linear but are formed from compliant materials such that they can be inserted into the tissue sample 220a along a non-linear path that may include tight turns unsuitable for traditional glass fibers.

The devices 100a and 100b can be introduced into the tissue sample 220a, and also can also be inserted through the nerve fascicle 222a. As a result, the devices 100a and 100b can be configured to deliver neural stimulation pulses directly to nerve fibers within the nerve fascicle 222a. As described above, the devices 100a and 100b can each be configured to deliver or monitor stimulation pulses via multiple modalities, including optical stimulation (e.g., via optrodes such as the optrodes 112 of FIG. 1B) and electrical stimulation (e.g., via electrodes such as the electrodes 111 of FIG. 1B). In addition, as depicted in FIG. 2A, multiples instances of the device 100 can be used together to create more specific focal points of light stimulation or to monitor light from overlapping volumes within the nerve fascicle 222a or elsewhere within the tissue sample 220a.

Figure 2B:
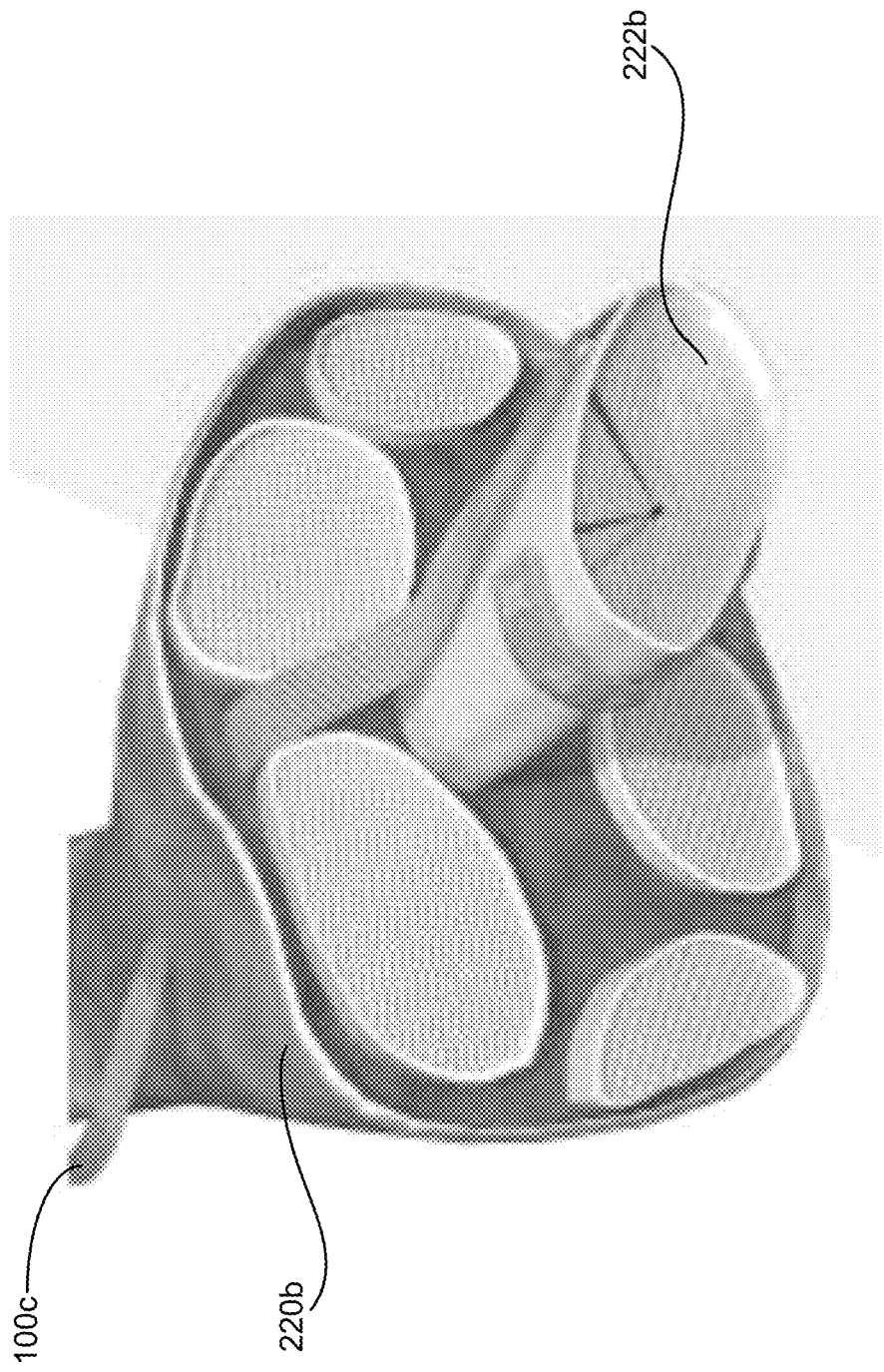
FIG. 2B illustrates a second example precision optogenetic interface, according to an illustrative implementation.

FIG. 2B illustrates a second example precision optogenetic interface, according to an illustrative implementation. The components are similar to those illustrated in FIG. 2A, and similar reference numerals refer to similar elements. As shown, a single instance of the device 100 shown in FIG. 1A (labeled 100c in FIG. 2B) can be inserted into a tissue sample 220b. In this example, the tissue sample 220b is nerve tissue including several nerve fascicles, such as the nerve fascicle 222b. The device 100c can be introduced into the tissue sample 220a, and can be wrapped around the nerve fascicle 222b such that it remains in contact with (or at least in close proximity to) a radial edge of the nerve fascicle 222b. As a result, the device 100c can be configured to deliver neural stimulation pulses or to monitor a response of the nerve tissue from a plurality of directions around the edge of the nerve fascicle 222b.

As described above, the device 100c can each be configured to deliver or monitor stimulation pulses via multiple modalities, including optical stimulation (e.g., via optrodes such as the optrodes 112 of FIG. 1B) and electrical stimulation (e.g., via electrodes such as the electrodes 111 of FIG. 1B). It should also be understood that, although only a single device 100c is illustrated in FIG. 2B, in some implementations multiples instances of the device 100 can be used together to create more specific focal points of light stimulation or to monitor light from overlapping volumes within the nerve fascicle 222b or elsewhere within the tissue sample 220b.

Figure 3:
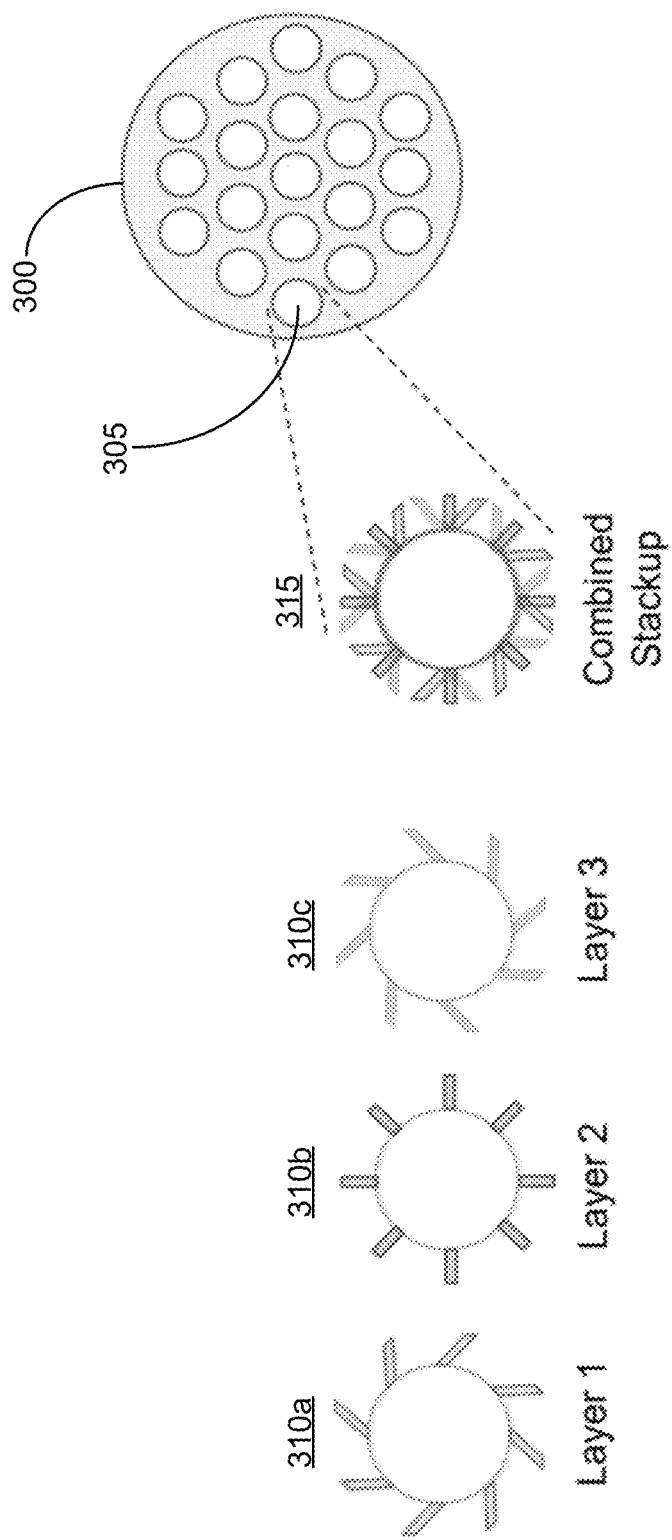
FIG. 3 illustrates an example intraneural structure having pores, according to an illustrative implementation.

FIG. 3 illustrates an example intraneural structure 300 having pores 305, according to an illustrative implementation. A section of nerve tissue (such as the tissue samples 220a and 220b illustrated in FIGS. 2A and 2B) can be severed, and the intraneural structure 300 can be inserted into the severed section of nerve tissue. In some implementations, axons may regenerate through the pores 305 after insertion of the intraneural structure 300 into the nerve. Thus, the intraneural structure 300 can be referred to as a "sieve" device. In some implementations, the intraneural structure 300 can be or can include an instance of the device 100 shown in FIGS. 1A and 1B. For example, each pore 305 may correspond to one or more electrodes or optrodes, which may be arranged to wrapper around the pores or to extend along the lengths of channels that define the pores within the intraneural structure 300.

The intraneural structure 300 can include pores with geometries that allow the intraneural structure to deliver and monitor light from intersecting beams of light. For example, thin layers of optrodes with fixed-directional apertures can be stacked adjacent to one another to create discrete multi-directional apertures to steer light in multiple directions. An example of this is shown by the patterns 310a-310c associated with the layers 1-3 on the left-hand side of FIG. 3. As shown, the patterns 310a-310c can effectively be combined to form the pattern 315 in the region of the combined stack of the layers. In some implementations, multiple pores can be used to sub-divide larger tissue volumes and create sculpted light patterns within each sub-volume.

Figure 4B:
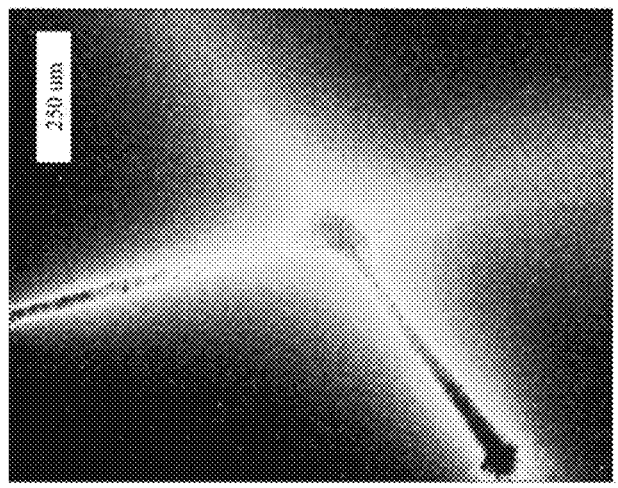
FIG. 4B shows an activation pattern simulated in FIG. 4A in actual optical scattering media, according to an illustrative implementation.
Figure 4A:
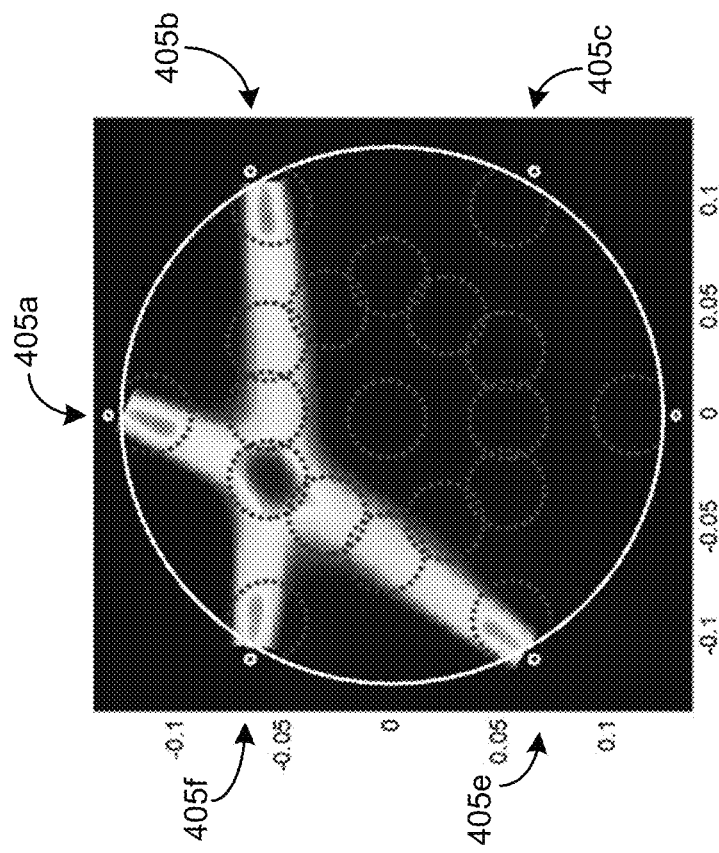
FIG. 4A illustrates a simulation of directional light patterns that can be constructed from six optrode sites 405a-405f with three directional beams, according to an illustrative implementation.

FIG. 4A illustrates a simulation of directional light patterns that can be constructed from six optrode sites 405a-405f with three directional beams, according to an illustrative implementation. The optrode sites 405a-405f are symmetrically positioned around the edge of a circular cross-section of tissue representing a nerve fascicle. The circles shown in broken lines represent 19 unique activation areas that can be targeted using the optrode sites 405a-405f. One particular pattern is illustrated in FIG. 4A based on Monte Carlo simulations, however any of the other activation regions could also be targeted using these same optrode sites 405a-405f. FIG. 4B shows the activation pattern simulated in FIG. 4A in actual optical scattering media, which was selected to have scattering parameters similar to biological tissue.

Figure 5:
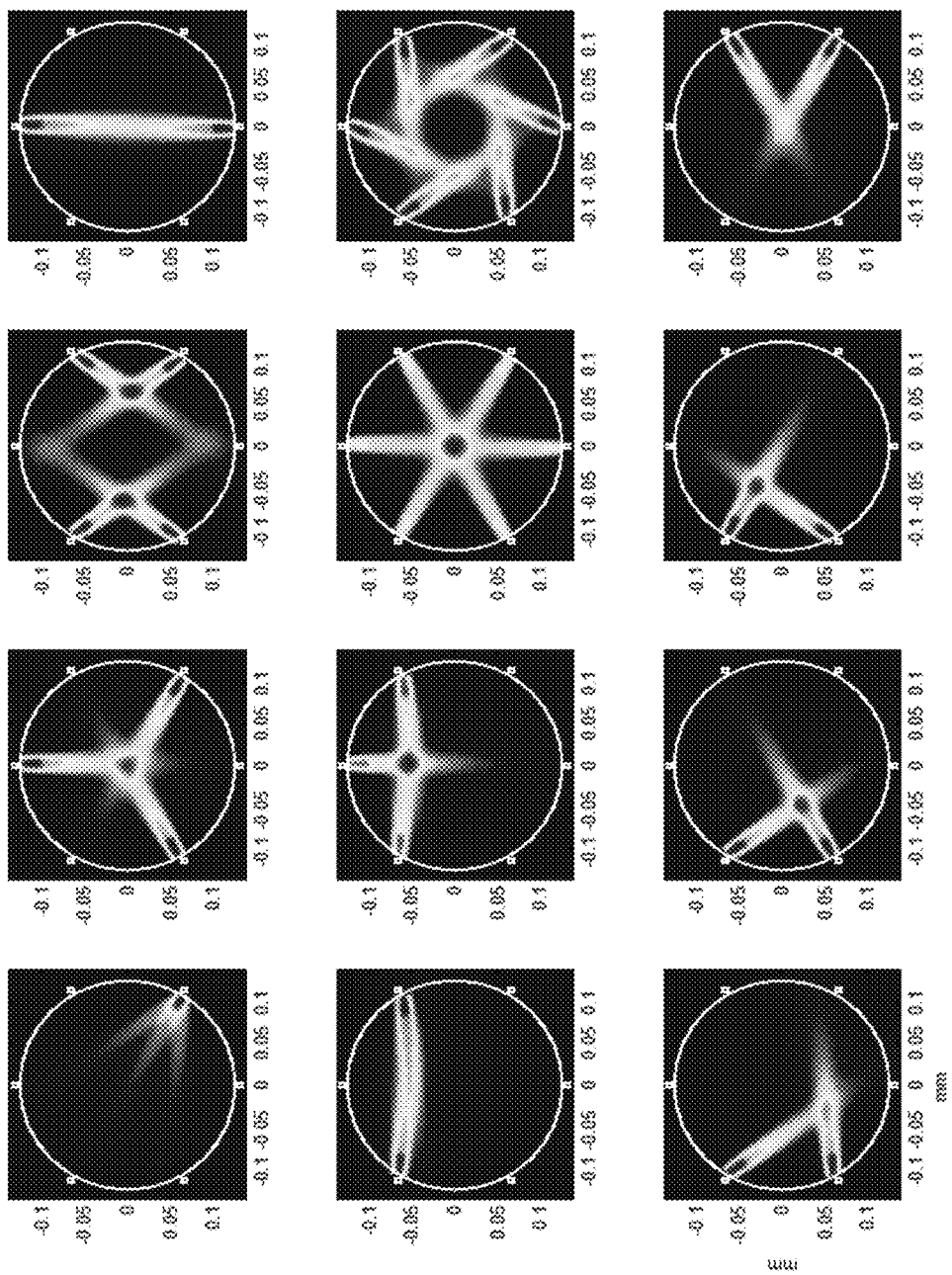
FIG. 5 illustrates various example light patterns that can be generated using the devices described in this disclosure, according to an illustrative implementation.

FIG. 5 illustrates various example light patterns that can be generated using the devices described in this disclosure, according to an illustrative implementation. These patterns can result from both wrapping optrodes around tissue, as shown in FIG. 2B, and from fabricating such optrodes in patterns where beams can intersect, for example as described above in connection with FIG. 3. In some implementations, light beam intersections can also be created by optrodes in adjacent devices as shown in FIG. 2A, for example.

CONCLUSION

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An intraneural device, comprising:
a pore configured to receive a structure in a nerve tissue sample;
a first stack of flexible waveguide materials providing a first plurality of compliant optrodes, a second stack of flexible waveguide materials providing a second plurality of compliant optrodes, and a third stack of flexible waveguide materials providing a third plurality of compliant optrodes, each of the first plurality of compliant optrodes comprising a respective first optical interface, each of the second plurality of compliant optrodes comprising a respective second optical interface, and each of the third plurality of compliant optrodes comprising a respective third optical interface,
wherein each of the first and second stacks of flexible waveguide materials has a thickness of less than about 25 microns, and wherein each of the first and second stacks of flexible waveguide materials comprises at least:
(i) an electrode defined by a metal layer;
(ii) a core comprising a poly(methyl methacrylate) (PMMA) material having a first index of refraction; and
(iii) a cladding comprising a fluoropolymer material coupled to the PMMA material of the core, the cladding having a second index of refraction different from the first index of refraction; and
a fourth optical interface that receives light corresponding to an optical response from the structure in the nerve tissue sample;
wherein the difference between the first index of refraction and the second index of refraction is such that light remains in the core while the first and second stacks of flexible waveguide materials are wrapped around the pore;
wherein each of the first and second stacks of flexible waveguide materials is capable of routing light within the core and is wrapped around the pore such that the first and second optical interface emit light in the pore when the structure in the nerve tissue sample having a radius of less than about 300 microns is received by the pore; and
wherein the respective first optical interface of each of the first plurality of compliant optrodes, the respective second optical interface of each of the second plurality of compliant optrodes, and the respective third optical interface of each of the third plurality of compliant optrodes are configured to selectively emit focused beams of light that create a plurality of unique focal points within the pore.

2. The intraneural device of claim 1, wherein each of the first, second, and third stacks of flexible waveguide materials each comprise at least one mechanical property selected to substantially match a corresponding modulus of the nerve tissue sample.

3. The intraneural device of claim 1, wherein the first, second, and third stacks of flexible waveguide materials each provides optical stimulation to at least a portion of the nerve tissue sample by projecting light transmitted through the first and second stacks of flexible waveguide materials.

4. The intraneural device of claim 1, wherein the electrode provides an electrical interface for at least one of the first, second, and third stacks of flexible waveguide materials.

5. The intraneural device of claim 1, wherein the pore is configured to receive an axon within the nerve tissue sample.

6. The intraneural device of claim 5, wherein light is emitted into the axon when the axon is received by the pore.

7. The intraneural device of claim 1, further comprising one or more microfluidic structures.

8. An intraneural device, comprising:
a pore configured to receive a structure in a nerve tissue sample, the structure having a radius of less than about 300 microns;
a stack of a plurality of layers, each of the plurality of layers defining a plurality of optrodes, each of the plurality of optrodes having a respective directional aperture, each optrode of the plurality of optrodes configured to selectively transmit a respective directional beam via the respective directional aperture of the layer, such that the respective directional beams transmitted by the optrode emit light in a direction that is non-orthogonal to a perimeter of the pore, wherein each layer of the plurality of layers has a thickness of less than about 25 microns, and wherein each layer comprises at least:
(i) an electrode defined by a metal layer;
(ii) a core comprising a poly(methyl methacrylate) (PMMA) material having a first index of refraction; and
(iii) a cladding comprising a fluoropolymer material coupled to the PMMA material of the core, the cladding having a second index of refraction different from the first index of refraction; and
an optical interface that receives light corresponding to an optical response from the structure in the nerve tissue sample;
wherein the difference between the first index of refraction and the second index of refraction is such that light remains in the core while the stack of the plurality of layers is wrapped around the pore; and
wherein the stack of the plurality of layers is capable of routing light within the core of each layer and is wrapped around the pore such that the respective directional beams create at least one unique focal point within the pore.

9. The intraneural device of claim 8, wherein the respective directional aperture of each of the plurality of layers is configured to provide optical stimulation to at least a portion of the nerve tissue sample by projecting light transmitted through each of the plurality of layers.

10. The intraneural device of claim 8, wherein the electrode defined by the metal layer of each of the plurality of layers is configured to provide a respective electrical interface.

11. The intraneural device of claim 8, further comprising one or more microfluidic structures.

* * * * *